Aug. 20, 1974 F. A. G. VAN ENGELEN Plant Pat. 3,596
ROSE PLANT
Filed March 15, 1973
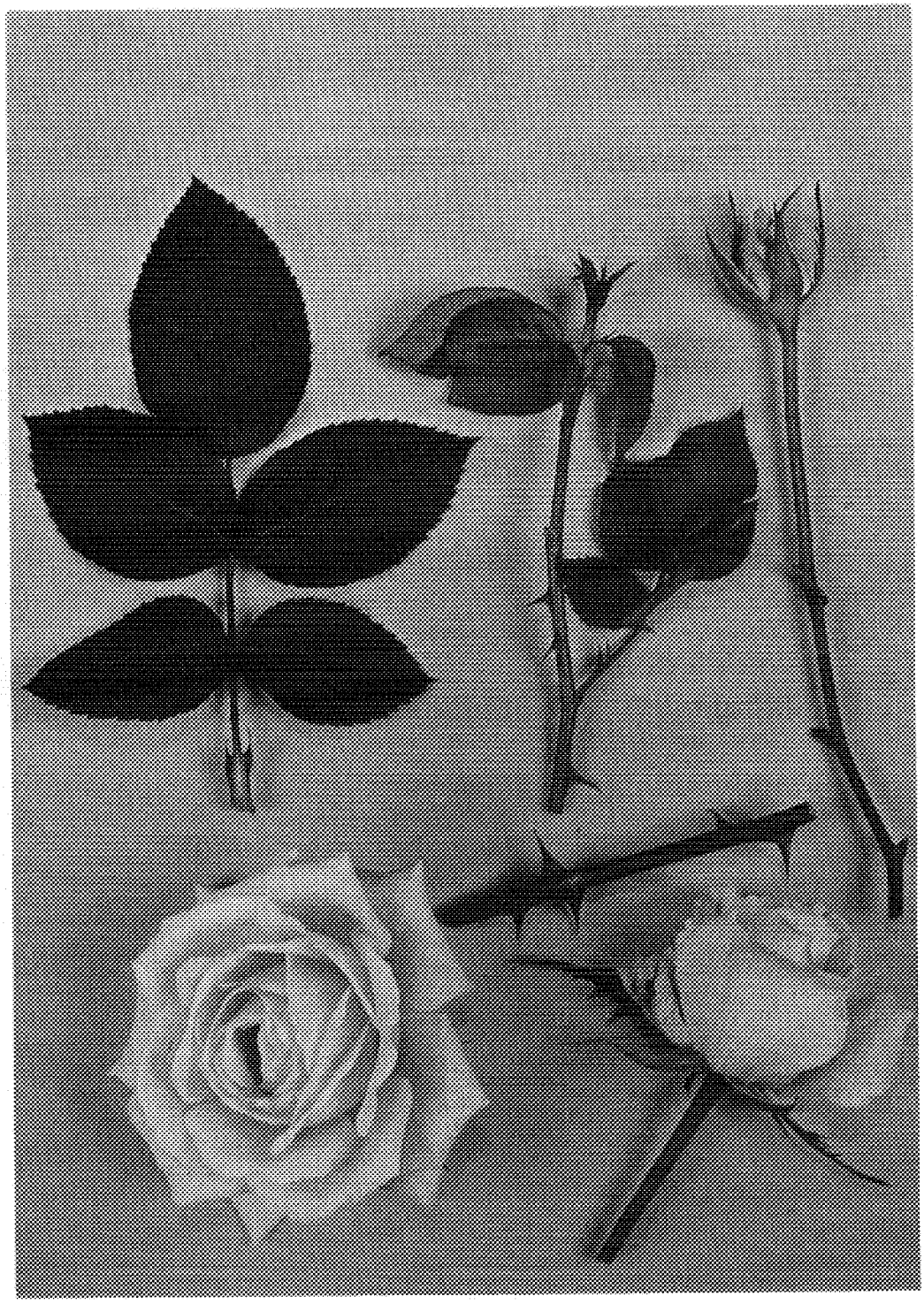

United States Patent Office

Plant Pat. 3,596
Patented Aug. 20, 1974

3,596
ROSE PLANT

Floor A. G. van Engelen, De Kwakel, Netherlands, assignor to Math. Tantau

Filed Mar. 15, 1973, Ser. No. 341,790
Int. Cl. A01h 5/00
U.S. Cl. Plt.—24 1 Claim This invention relates to a new and distinct variety of rose plant of the floribunda class. It is a sport of the variety "Belinda" which is the subject of United States patent application Ser. No. 199,506, filed Nov. 17, 1971, now P.P. No. 3,382.

This rose variety of the floribunda class bears clear yellow flowers and is a vigorous plant which produces more cut flowers in the greenhouse than other varieties of which I am aware. It distinguishes from its parent variety as well as from all other varieties of which I am aware, in the following features:

1. A medium sized flower, long lasting as a cut flower in a clear yellow color with a good fragrance.
2. Abundant production of medium long cut flowers repeating very rapidly.
3. For cut flower purposes side buds have to be removed.
4. It may be forced very early and it produces very firm stems.
5. The color is very bright and very intense.
6. Cut flowers may be stored in a cool environment for several days without loosing any of their intensity.

Asexual reproduction of my new variety by budding, as performed at Uetersen, Germany, shows that the aforementioned characteristics and distinctions come true to form and are established and transmitted through succeeding propagations.

The accompanying drawing shows typical specimens of the vegatative growth and flowers of my new variety in different stages of development, depicted in color as nearly true as it is reasonably possible to make the same in a color illustration of this character.

The following is a detailed description of my new rose variety with color terminology in accordance with *Royal Horticultural Society Color Chart*, except where ordinary dictionary significance of color is indicated.

Parentage: Sport
*Parent variety.*—Belinda.
Classification:
*Botanic.*—*Rosa hybrid.*
*Commercial.*—Floribunda.

FLOWER

Observations were made at Uetersen, Germany in October, from plants in a greenhouse.

Blooming Habit: Recurrent—continuous.
Bud:
*Size.*—One-third inch when petals start to unfurl.
*Form.*—Long, pointed.
*Color.*—When sepals first divide—green-yellow, 1 Group A. When half blown; inside of petals—yellow, 12 Group B, reverse of petals—yellow, 12 Group B.
*Sepals.*—Color: Outer surface—green, 138 Group B. Inner surface—gray-green, 191 Group A. Three appendaged sepals normally appendaged.
*Receptacle.*—Color: Yellow-green, 145 Group D. Shape: Funel. Size: Small. Surface: Smooth.
*Peduncle.*—Length: Medium. Surface: Smooth. Color: Medium green. Strength: Erect.
*Opening.*—Slowly.

Bloom:
*Size.*—Medium. Average size when fully expanded, three inches.
*Borne.*—Several together, in clusters. Clusters—pyramidal.
*Stems.*—Medium, normal.
*Form.*—When first open, high center. Permanence—retains its form to the end, quill fashion.
*Petalage.*—Number of petals under normal conditions, 28–32.
*Color.*—Center of flowers: Upper side of petals—yellow, 12 Group A. Reverse side of petals—yellow, 12 Group B. Outer petals: Upper side of petals—yellow, 12 Group A. Reverse of petals—light yellow, 12 Group B. Base of petals: Yellow, 13 Group A. General tonality from a distance—yellow. No variegations.
*Discoloration.*—The yellow color is constant.
*Fragrance.*—Moderate.
Petals:
*Texture.*—Soft.
*Surface.*—Inside—satiny. Reverse—satiny.
*Shape.*—Oval.
*Form.*—Edges slightly quilled.
*Arrangement.*—Imbricated.
*Petaloids in center.*—Few, small.
*Persistence.*—Drop off cleanly.
*Lastingness.*—On the plant—long. As cut flower—long.
Reproductive Parts:
*Stamens, anthers.*—Medium, many. Color—yellow. Arrangement—regular around styles.
*Stamens, filaments (threads).*—Long. Color—Yellow.
*Pollen.*—Golden yellow.
*Styles.*—Columnar, of uneven lengths.
*Stigmas.*—Color—yellow.
*Ovaries.*—All enclosed in calyx.
Fruit:
*Form.*—Round headed.
*Surface.*—Smooth.
*Color at maturity.*—Orange.
*Sepals.*—Recurved.

PLANT

Form: Bush.
Growth: Vigorous.
Foliage: Number of leaflets on normal mid-stem leaves, 5.
*Size.*—Medium.
*Quantity.*—Normal.
*Color.*—New foliage: Green, 137 Group A. Old foliage: Green, 139 Group A.
Leaflets:
*Shape.*—Oval pointed.
*Texture.*—Upper side—smooth. Under side—smooth. Ribs and veins—ordinary.
*Edge.*—Serrated.
*Serration.*—Single, sharp.
*Petiole (rachis).*—Color—green. Underside—prickles.
*Stipules.*—Medium, serrated.
*Desease resistance.*—Resistant to mildew under normal growing conditions at Uetersen, Germany.
Wood:
*New wood.*—Color—light green. Bark—smooth.
*Old wood.*—Color—Bark—smooth.
Prickles:
*Quantity.*—On main stalks—ordinary. On laterals—few.
*Form.*—Narrow base, long, straight.
*Color.*—When young—green and red.
*Position.*—Irregular.

Small Prickles:

*Quantity.*—On main stalks—few.

*Color.*—Brown.

Habit and growth are similar to the greenhouse variety of "Belinda," except that the color of the blooms is constant yellow and the foliage is a darker green without the reddish gleam of "Belinda." The blossoms average about four less petals and the foliage is somewhat more blunt than that of "Belinda."

I claim:

1. A new and distinct variety of rose plant of the floribunda class, substantially as herein shown and described, characterized particularly as to novelty by the unique combination of a vigorous bush having fast repeating habit of growth of medium size, double flowers of a shining yellow color, outstanding as a medium sized cut flower.

No references cited.

ROBERT E. BAGWILL, Primary Examiner